United States Patent [19]

Dubois, deceased et al.

[11] 4,178,513

[45] Dec. 11, 1979

[54] ART OBJECT ANALYZER

[75] Inventors: Jaques Dubois, deceased, late of Menlo Park, Calif.; Hans R. Zulliger, Portola Valley, Calif.

[73] Assignee: Nuclear Semiconductor, Mountain View, Calif.

[21] Appl. No.: 870,143

[22] Filed: Jan. 17, 1978

[51] Int. Cl.² .............................................. H05G 1/62
[52] U.S. Cl. ..................................... 250/491; 250/272
[58] Field of Search ........................ 250/272, 490, 491

[56] References Cited

U.S. PATENT DOCUMENTS

| | | | |
|---|---|---|---|
| 3,105,901 | 10/1963 | Ladell | 250/277 CH |
| 3,628,021 | 12/1971 | MacDonald | 250/505 |

*Primary Examiner*—Craig E. Church

[57] ABSTRACT

An apparatus for analyzing certain properties of an object with a beam of radiation capable of emitting fluorescent x-rays by (1) aligning a pivotally mounted radiation-emitting generator with a pivotally mounted radiation detector relative to a specific point on the object by providing for a beam of visible light to be separately directed from the generator and detector, (2) generating and projecting a beam of radiation against a selected portion of the object, which includes the points to be analyzed, causing the object point to become stimulated to emit its own radiation, (3) detecting this object-emitted beam of radiation by the detector and (4) analyzing the spectrum of the detected beam.

7 Claims, 4 Drawing Figures

4,178,513

ART OBJECT ANALYZER

FIELD OF INVENTION

This invention relates to an apparatus which makes use of fluorescent analysis to analyze an object, and more particularly the apparatus makes use of the x-ray energy levels to analyze various properties of the object. The invention teaches a means for properly aligning an x-ray or other radiation generator with radiation detector relative to a point on the object by substituting a beam of visible light for the beams of generated and detected radiation during alignment so that a collimated beam of radiation projected on an object by the generator will result in an emitted beam of radiation being detected by the radiation detector.

DESCRIPTION OF THE PRIOR ART

Several prior art references disclose means for aligning two or more electromagnetic energy generators with each other. For example, U.S. Pat. No. 3,117,480 (Peddinghaus) and U.S. Pat. No. 3,194,626 (Hoffmann) both teach adjustable alignment means which make use of a pair of angularly situated light beams. Various prior art references have substituted a visible light beam for an x-ray beam when aligning an x-ray generator or other electromagnetic generator with an object and some prior art have even projected a visible light beam on the x-ray generator side of a collimator so that the operator of the apparatus can determine the cross-sectional dimensions of the x-ray or other radiation beam by observing a visible light beam for which the operator is able to determine its cross-sectional dimensions.

However, there is still a need in the art for an apparatus equipped with means for properly aligning an x-ray or other radiation generator with a radiation detector relative to some specific point on an object such that not only can the cross-sectional dimensions of the radiation beam generated by the generator be determined, but the cross-sectional dimensions of the radiation beam detected by the detector can also be determined.

SUMMARY OF THE INVENTION

In view of this remaining need in the art for an apparatus with means for aligning a radiation detector with radiation-emitting generator and for determining the cross-sectional dimensions of not only the generated radiation beam but also the radiation beam detected by the detector, we have found a means for properly aligning a radiation-emitting generator with a radiation detector in such a manner that the cross-sectional dimensions of both the generated beam and the detected energy beam can be determined. Accordingly, we have devised an apparatus which comprises a pivotally mounted radiation-emitting generator and a pivotally mounted radiation detector, with the generator and detector each provided with alignment means which comprise independent light sources which have been substituted for x-ray or other radiation beams where the independent light sources are each focused onto the object to be analyzed in accordance with the invention in such a manner that the generator and detector are indicated as being in proper alignment with each other when their independent visible light beams coincide with each other at some point on the object.

BRIEF DESCRIPTION OF THE DRAWINGS

The advantages and characteristic features of the subject invention will be in part apparent from the accompanying drawings, and in part pointed out in the following detailed description of the invention in which reference will be made to the accompanying drawings wherein the reference numerals designate corresponding parts, and wherein.

DETAILED DESCRIPTION OF THE PREFERRED EMBODIMENTS

Figure 1:
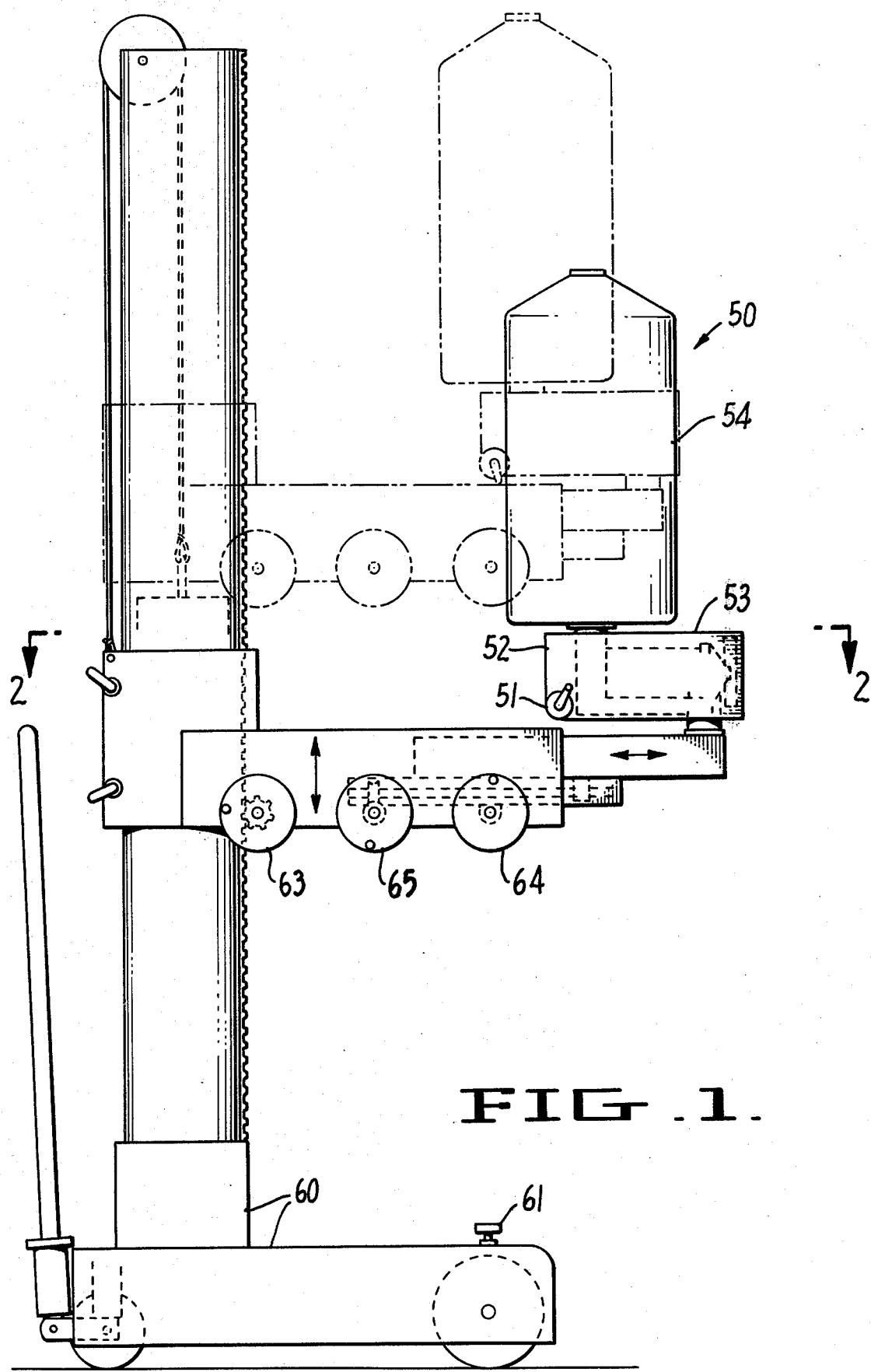
FIG. 1 is a side view of the object analyzer mounted on a movable cart.

FIG. 1 illustrates a side view of the object analyzer 50 mounted on a movable cart 60 which has a parking brake 61. Analyzer 50 is equipped with a focusing wheel 51 which, when in operation, causes radiation-emitting generator 1 and radiation detector 2 (enclosed in housing portion 53 and described subsequently with respect to FIG. 2) to be pivoted about points 11 and 21, respectively (see FIG. 2 description). Analyzer 50 is equipped with a protective enclosure 52 to protect the analyzer's operators and others from becoming exposed to humanly undesirable rays such as x-rays. Movable cart 60 is equipped with a vertical carriage 63 to allow for the vertical movement of analyzer 50 while mounted on cart 60. Lateral carriage 64 provided on cart 60 allows for lateral movement of analyzer 50 while mounted on cart 60 and longitudinal carriage 65 is provided on cart 60 to provide for longitudinal movement of analyzer 50 while positioned on cart 60. Carriages 63, 64 and 65 operate to allow analyzer 50 to be movable about its x, y and z axes. Analyzer is also provided with cooling means located in housing portion 54.

Figure 2:
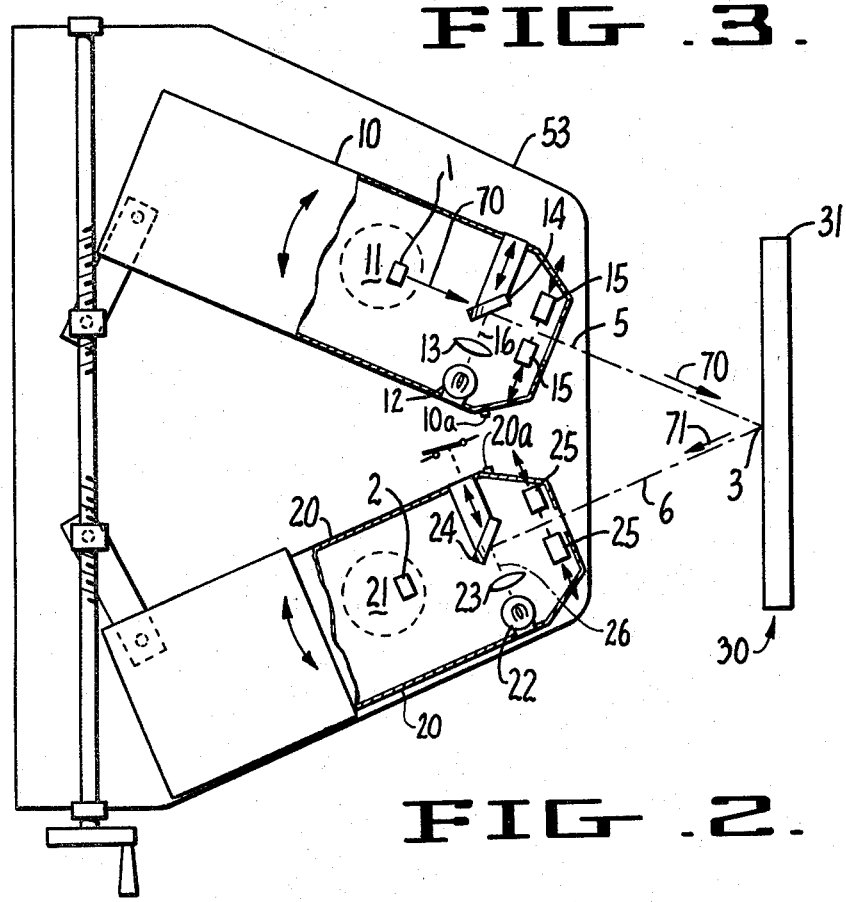
FIG. 2 is a partially schematic view of the object analyzer incorporating one embodiment of the present invention.

FIG. 2 is a partially schematic top view of a radiation-emitting generator 1 and a radiation detector 2 which are in proper alignment with each other relative to a point 3 on object 30. Housing unit 10, pivotally mounted in its horizontal plane to pivot about point 11, encloses a light source 12, a lens 13, a tiltably mounted retractable reflective surface 14 located along generator radiation path 5, collimator 15 and radiation-emitting generator 1. Housing unit 20, pivotally mounted in its horizontal plane to pivot about point 21 and adjacent to housing 10, encloses light source 22, lens 23, tiltably mounted retractable reflective surface 24, located along detector radiation path 6, collimator 25 and radiation detector 2.

When generator 1 and detector 2 are being aligned with each other, light source 12 is energized to produce light beam 16 which is focused by lens 13 onto reflective surface 14 which is tilted at a 45° angle relative to beam 16 to reflect beam 16 along a portion of radiation path 5 and through collimator 15 while housing 10 is being pivoted about point 11 until visible beam 16 from source 12 impinges upon an area of object 30 which includes point 3 where object 30 is located between ¼ inch and 6 inches from housing 53. When beam 16 illuminates an area of object 30 which includes point 3, light source 22 is energized to produce beam 26 which is focused by lens 23 onto reflective surface 24. Surface 24 is tiltably mounted at a 45° angle to beam 26 to reflect beam 26 along a portion of radiation path 6 and through collimator 25 while housing 20 is being pivoted about point 21 until visible beam 26 from source 22 impinges upon object 30 at point 3. When visible beams 16 and 26 coincide on an area of object 30 which includes point 3, as illustrated in FIG. 2, radiation-emitting generator 1 and the radiation detector 2 are said to be properly aligned with each other.

Generator 1 and detector 2 may be aligned in the above manner at any point on object 30. That is, point 3 may be anywhere on the surface of object 30. Point 3 may also be a point beyond the surface of object 30. For example, if object 30 were a painting on a canvas 31, it may be desirable to align generator 1 and detector 2 relative some point on the canvas 31 rather than the surface of the painting 30. This will be the case when the operator is interested in making a determination regarding the canvas on which the painting is done rather than making a determination about the painting itself. Since generator 1 and detector 2 are pivotally mounted about their horizontal axes, generator 1 and detector 2 may be rotated to become properly aligned with each other relative to some point located into the depth of object 30, for example, at some point on canvas 31. This will be done by aligning the generator 1 and detector 2 with a point on the surface of object 30 which will correspond to a point on canvas 31 to be analyzed. An appropriate filter (discussed subsequently with respect to FIG. 4) may be inserted along generator radiation path 5 to permit the necessary wavelengths of radiation to pass to object 30 in order to penetrate the depth of object 30 to reach an area on canvas 31.

Once generator 1 and detector 2 are properly aligned with each other relative to a point 3 on object 30 or some point corresponding to a point on canvas 31, light sources 12 and 22 are both de-energized and retractable surfaces 14 and 24 are removed from the radiation paths 5 and 6 of generator 1 and detector 2, respectively. Generator 1 is then energized to generate a beam of radiation 70 (subsequently described in FIG. 3) which passes along energy path 5 of FIG. 2 and impinges upon object 30 at an area which includes point 3. Once beam 70 strikes object 30 at an area including point 3, point 3 is stimulated to emit a similar beam(s) of radiation 71 some of which will then be directed towards detector 2 and along radiation path 6 (see FIG. 2) and through collimator 25 (see FIG. 2) and be detected by detector 2.

Generator 1 need not be focused on a point on object 30 before detector 2 is so focused. That is, it may be desirable to focus detector 2 and beam 26 on a specific area of object 30 which includes point 3 prior to focusing generator 1 on the area. This is because beam 26 will usually have smaller cross-sectional dimensions than generator beam 16. Detector 2 need only be aligned with a small area including point 3 since detector 2 need only detect some of the emitted radiation such as x-rays from this area in order to get an analysis of point 3. Where detector 2 is aligned with point 3 before aligning generator 1, generator 1 will then only need be focused upon an area of object 30 which includes point 3. That is, beam 16 usually having a larger cross-sectional dimension than beam 26, will coincide with beam 26 when beam 16 illuminates an area larger than that illuminated by beam 26, but such area must include the area illuminated by beam 26. When this is done, any radiation emitted by generator 1 will impinge upon an area on object 30 which will include the desired area to be analyzed (that of point 3) and some of the radiation emitted by this area will move in the direction of detector 2 and be detected.

It is also important to note that generator 1 and detector 2 may become aligned relative to some point on an object without using visible light sources to illuminate the object area. That is, generator 1 and detector 2 may each be provided with a pointer, located along their respective radiation paths, to located the desired area of object 30 to be analyzed. In such an instance, object 30 may be illuminated by the ambient light in the room in which the object is located.

Figure 3:
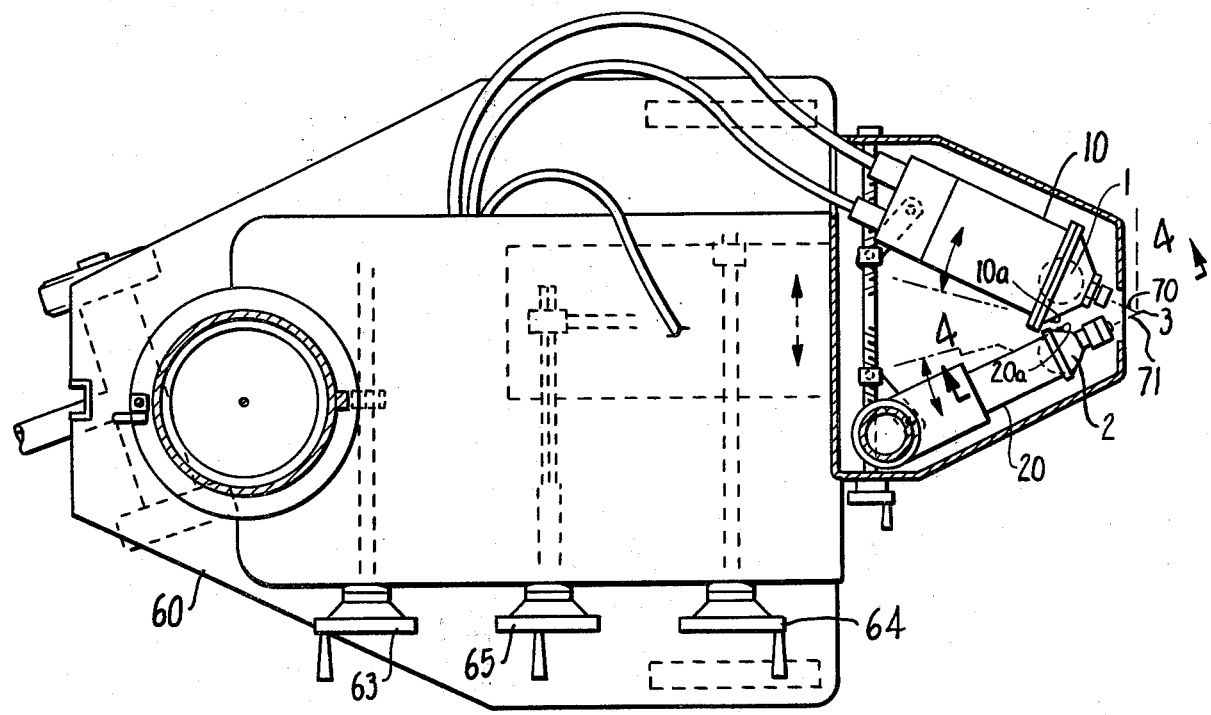
FIG. 3 is a top plan view of the object analyzer illustrating the embodiment of FIG. 2.

A fiberoptic bundle may be mounted along the external side of housing 10 or housing 20 at either point indicated by reference numerals 10a and 20a on FIG. 2 and FIG. 3. This fiberoptic bundle will enable the analyzer operator to photograph and/or view the area of object 30 which is being analyzed.

FIG. 3 is a top plan view of the inventive embodiment described above in FIG. 2, illustrating radiation-emitting generator 1 and radiation detector 2 in proper alignment with each other relative to point 3 on object 30. Generator 1 produces radiation beam 70 which travels along radiation path 5 (see FIG. 2) and onto object 30 to fluoresce an area of object 30 which includes point 3 whereupon point 3 and its surrounding area which is contacted by beam 70 is stimulated by beam 70 to emit beam 71. Beam 71 then travels in the direction of and along path 6 (see FIG. 2) and is detected by detector 2. The spectrum of beam 71 is electronically analyzed by suitable electronic means, part of which are located in housing 20 and parts of which are externally housed to determine various properties about point 3 of object 30.

Figure 4:
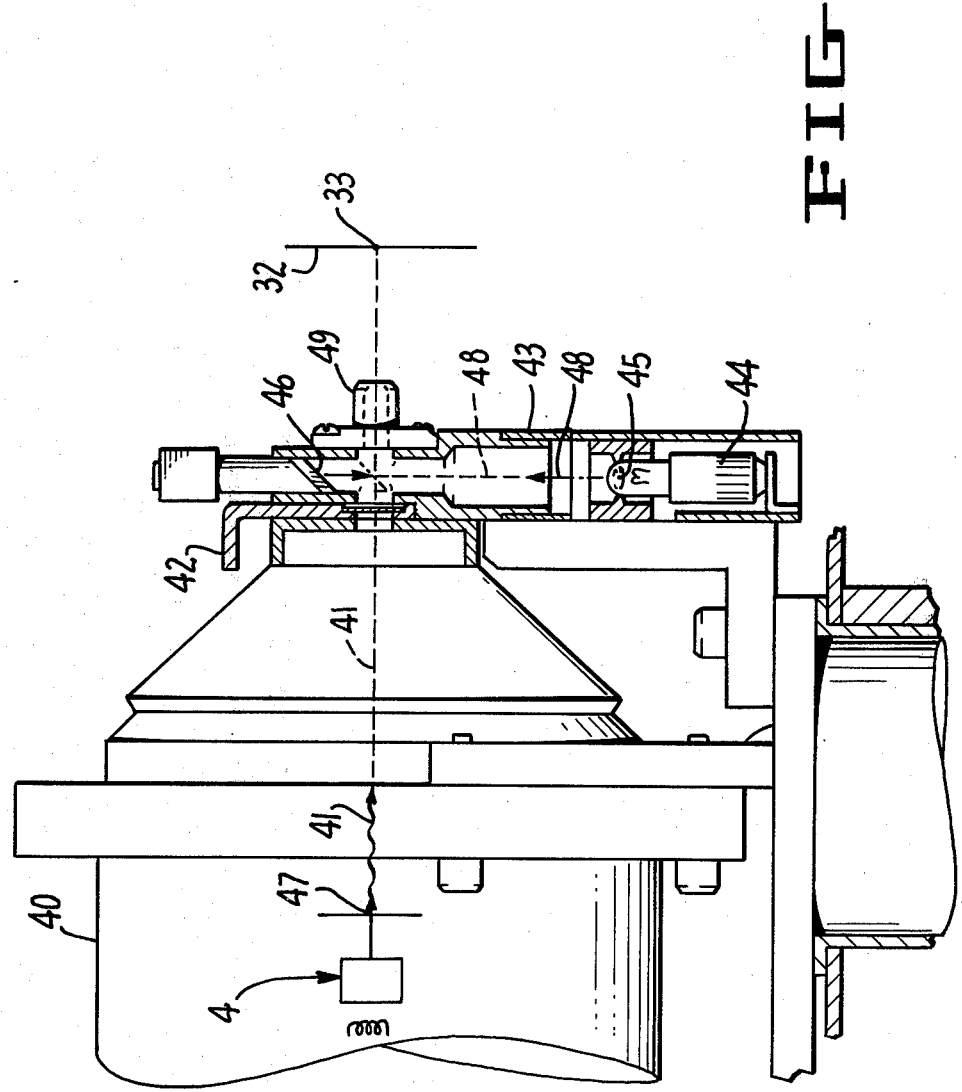
FIG. 4 is a side elevational view of the invention incorporating another embodiment of the present invention.

FIG. 4 is a side elevational view of one embodiment of the invention with an x-ray generator 4 mounted in housing 40 with x-ray path 41 directed towards object 32. Abutting generator 4 along path 41 is a filter 42 and an x-ray generator alignment assembly 43. Assembly 43 has a light source 44 with a built-in lens 45 to focus light from source 44 onto a tiltably mounted mirror 46. Mirror 46 is mounted at a 45° angle relative to source 44 so that light from source 44 upon striking mirror 46 will be reflected by mirror 46 at a 45° angle of reflection to pass through x-ray path 41 and onto an area of object 32 which includes point 33.

When in operation generator 4 is aligned with point 33 in a manner similar to that described for aligning generator 1 with point 3 in FIG. 2. That is light beam 48 from source 44 is focused by built-in lens 45 onto mirror 46 and mirror 46 reflects light beam 48 through path 41 and collimator 49 and onto object 32. Generator 4 is constantly being rotated about its horizontal axis by means of focusing wheel 51 (FIG. 1) so that beam 48 will impinge upon an area of object 32 which includes point 33.

When beam 48 is properly focused upon object point 33 an x-ray detector (not shown but similar to the radiation detector 2 of FIG. 2) is then aligned with generator 4 relative to point 33 in the same manner as was described above in FIG. 2. Once generator 4 is properly aligned with an x-ray detector (not shown), light 44 and a similar detector light source (not shown) are de-energized, mirror 46 and a similar mirror in an x-ray detector assembly (not shown) are removed from along path 41 and a similar detector path as path 6 of FIG. 3 and generator 4 is energized to produce x-rays 47. X-rays 47 pass through a filter 42, which may be molybdenum, and continues along path 41 to fluoresce an area of object 32 which includes point 33. Once x-ray 47 impinges upon point 33, point 33 and the surrounding area are stimulated to emit its own x-rays (as described in FIG. 3) which then move along a path toward an x-ray detector (see FIGS. 2 and 3) where some of the emitted x-rays are detected. The spectrum of the detected x-ray is then analyzed by suitable electronic means 20 to determine certain properties about point 33 which may also be determinative of certain properties of the entire object 32.

Filter 42 operates to adjust or filter certain wavelengths of x-ray 47 or of other radiation rays. Filter 42 may be varied depending on what one wishes to determine about a particular object under analysis. That is different filters penetrate different depths of an object, exciting different energy levels of an object. The higher the excitation voltage produced by an x-ray impinging upon an object, the deeper the x-ray has penetrated the object.

The terms and expressions which have been employed here are used as terms of description and not of limitations, and there is no intention, in the use of such terms and expressions, of excluding equivalents of the features shown and described, or portions thereof, it being recognized that various modifications are possible within the scope of the invention claimed.

What is claimed is:

1. A method of analyzing an object with a beam of ionizing radiation comprising the steps of:
   (a) aligning an ionizing radiation-emitting generator, mounted in a generator housing, with an ionizing radiation detector, mounted in a detector housing, emitting a beam of visible light from a visible light source mounted in said generator housing and directing said beam of visible light with a generator beam directing means onto a point on said object, emitting a beam of visible light from a light source mounted in said detector housing and directing said beam of visible light with a detector beam directing means onto said same object point, and pivoting said generator and said detector with respect to each other in a common plane until said detector visible light beam coincides with said generator visible light beam on said object point;
   (b) de-energizing said generator and said detector visible light sources and removing said generator and said detector beam directing means when said generator light beam coincides with said detector light beam;
   (c) generating a beam of ionizing radiation from said generator and projecting said beam onto said object including said point of coincidence; and
   (d) detecting a beams of ionizing radiation with said detector where said beam is emitted by said point of coincidence when said generator radiation beam contacts said point of coincidence.

2. A method in accordance with claim 1 wherein the steps of generating a beam of ionizing radiation comprises the step of generating x-rays.

3. An apparatus for analyzing an object with a beam of ionizing radiation comprising:
   a generator, mounted in a housing, for emitting a beam of ionizing radiation along a radiation path in the direction of said object to be analyzed;
   a detector, mounted in a housing, for detecting ionizing radiation along a radiation path;
   means for aligning said generator radiation path and said detector radiation path each, with respect to the other, and both relative to a point on said object to be analyzed such that a beam of ionizing radiation projected onto said object, including said point of said object, by said generator along said generator radiation path in the direction of said point, will stimulate said point on said object to emit ionizing radiation along said detector radiation path, said aligning means including a generator aligning means, having a visible light source mounted in said generator housing and means for directing light from said generator visible light source along said generator radiation path and onto said object including said point, and a detector aligning means, having a visible light source mounted in said detector housing and means for directing light from said detector visible light source along said detector radiation path and onto said object including said point.

4. An apparatus according to claim 3 wherein said generator aligning means further has a lens, a retractable reflective surface mounted in said generator housing with said lens, said reflective surface and said generator visible light source each being selectively alignable with respect to the others such that light from said generator visible light source is focused by said lens onto said retractable reflective surface and said light is reflected by said reflective surface along said generator radiation path and onto said object, and said detector aligning means further having a lens, a retractable reflective surface, mounted in said detector housing with said lens, said reflective surface and said detector visible light source each being selectively alignable with respect to the others such that light from said detector visible light source is focused by said lens onto said detector retractable reflective surface and said light is reflected by said reflective surface along said detector radiation path and onto said object.

5. Apparatus according to claim 4 wherein said generator and said detector reflective surfaces are mirrors and are each angularly displaced relative to a beam of visible light from said generator and said detector visible light sources respectively.

6. Apparatus according to claim 3 wherein the ionizing radiation beams emitted by said generator and detected by said detector are x-rays.

7. Apparatus according to claim 3 wherein said ionizing radiation-emitting generator and said ionizing radiation detector are each pivotally mounted about their respective vertical axes such that said generator and said detector are each freely adjustable about their respective vertical axes.

* * * * *